United States Patent
Izmailov et al.

(10) Patent No.: US 7,222,059 B2
(45) Date of Patent: May 22, 2007

(54) ELECTROPHORETIC TRACE SIMULATOR

(75) Inventors: Alexandre M. Izmailov, Etobicoke (CA); Thomas Yager, Mississauga (CA)

(73) Assignee: Siemens Medical Solutions Diagnostics, Tarrytown, NY (US)

( * ) Notice: Subject to any disclaimer, the term of this patent is extended or adjusted under 35 U.S.C. 154(b) by 320 days.

(21) Appl. No.: 10/295,964

(22) Filed: Nov. 15, 2002

(65) Prior Publication Data
US 2003/0120471 A1    Jun. 26, 2003

Related U.S. Application Data

(60) Provisional application No. 60/332,471, filed on Nov. 15, 2001.

(51) Int. Cl.
*G06F 17/50* (2006.01)
*C12Q 1/68* (2006.01)

(52) U.S. Cl. .................. 703/2; 703/12; 435/6
(58) Field of Classification Search ............ 703/2, 703/11, 12; 702/20; 435/6
See application file for complete search history.

(56) References Cited

U.S. PATENT DOCUMENTS

| 3,742,202 A | 6/1973 | Spreitzhofer |
| 4,329,591 A | 5/1982 | Fujiwara et al. |
| 4,363,705 A | 12/1982 | Hunyar et al. |
| 4,683,194 A | 7/1987 | Saiki et al. |
| 4,683,195 A | 7/1987 | Mullis et al. |
| 4,683,202 A | 7/1987 | Mullis et al. |
| 4,720,786 A | 1/1988 | Hara |
| 4,729,947 A | 3/1988 | Middendorf et al. |
| 4,795,699 A | 1/1989 | Tabor et al. |
| 4,800,159 A | 1/1989 | Mullis et al. |
| 4,811,218 A | 3/1989 | Hunkapiller et al. |
| 4,823,007 A | 4/1989 | Hanson |
| 4,849,513 A | 7/1989 | Smith et al. |

(Continued)

FOREIGN PATENT DOCUMENTS

DE    4405251    8/1994

(Continued)

OTHER PUBLICATIONS

Andersson, et al., "Adaptor-Based Uracil DNA Glycosylase Cloning Simplifies Shotgun Library Construction for Large-Scale Sequencing", *Analytical Biochemistry* 218: 300-308 (1994).

(Continued)

*Primary Examiner*—Thai Phan
(74) *Attorney, Agent, or Firm*—Brinks Hofer Gilson & Lione

(57) ABSTRACT

A simulated electrophoretic trace is prepared by first obtaining an input file containing an input base sequence comprising a string of letters (A, C, G and/or T) in an order corresponding to the input base sequence, and then modifying the input file using one or more functions to take into account perturbations associated with (1) changes in peak intensity as a function of base number; (2) peak shape as a function of base number; (3) peak skew; (4) spacing between peaks; (5) background; (6) noise; (7) spectral cross-talk; (8) instrumental effects and/or (9) gel electrophoresis effects to produce a modified file representing a simulated electrophoretic trace. The method may be performed using a specially adapted apparatus.

8 Claims, 12 Drawing Sheets

U.S. PATENT DOCUMENTS

| | | | |
|---|---|---|---|
| 4,855,225 A | 8/1989 | Fung et al. | |
| 4,865,968 A | 9/1989 | Orgel et al. | |
| 4,889,818 A | 12/1989 | Gelfand et al. | |
| 4,941,092 A | 7/1990 | Hara et al. | |
| 4,942,124 A | 7/1990 | Church | |
| 4,960,999 A | 10/1990 | McKean et al. | |
| 4,965,188 A | 10/1990 | Mullis et al. | |
| 4,982,326 A | 1/1991 | Kaneko | |
| 5,008,182 A | 4/1991 | Sninsky et al. | |
| 5,075,216 A | 12/1991 | Innis et al. | |
| 5,079,352 A | 1/1992 | Gelfand et al. | |
| 5,096,557 A | 3/1992 | Simons | |
| 5,108,179 A | 4/1992 | Myers | |
| 5,118,800 A | 6/1992 | Smith et al. | |
| 5,119,316 A | 6/1992 | Dam et al. | |
| 5,122,345 A | 6/1992 | Tabor et al. | |
| 5,124,247 A | 6/1992 | Ansorge | |
| 5,171,534 A | 12/1992 | Smith et al. | |
| 5,175,082 A | 12/1992 | Jeffreys | |
| 5,176,995 A | 1/1993 | Sninsky et al. | |
| 5,190,632 A | 3/1993 | Fujimiya et al. | |
| 5,207,880 A | 5/1993 | Middendorf et al. | |
| 5,213,673 A | 5/1993 | Fujimiya et al. | |
| 5,246,866 A | 9/1993 | Nasu et al. | |
| 5,268,486 A | 12/1993 | Waggoner et al. | |
| 5,273,632 A | 12/1993 | Stockham et al. | |
| 5,283,171 A | 2/1994 | Manos et al. | |
| 5,290,419 A | 3/1994 | Kambara et al. | |
| 5,308,751 A | 5/1994 | Ohkawa et al. | |
| 5,352,600 A | 10/1994 | Gelfand et al. | |
| 5,360,523 A | 11/1994 | Middendorf et al. | |
| 5,365,455 A | 11/1994 | Tibbetts et al. | |
| 5,418,149 A | 5/1995 | Gelfand et al. | |
| 5,419,825 A | 5/1995 | Fujii | |
| 5,427,911 A | 6/1995 | Ruano | |
| 5,453,355 A | 9/1995 | Birkenmeyer et al. | |
| 5,484,701 A | 1/1996 | Cocuzza et al. | |
| 5,502,773 A | 3/1996 | Tibbetts et al. | |
| 5,527,898 A | 6/1996 | Bauer et al. | |
| 5,584,983 A | 12/1996 | Pruyn | |
| 5,608,063 A | 3/1997 | Hobbs, Jr. et al. | |
| 5,614,386 A | 3/1997 | Metzker et al. | |
| 5,666,435 A | 9/1997 | Burgi et al. | |
| 5,667,971 A | 9/1997 | Hochberg | |
| 5,710,628 A | 1/1998 | Waterhouse et al. | |
| 5,712,476 A | 1/1998 | Renfrew et al. | |
| 5,733,729 A | 3/1998 | Lipshutz et al. | |
| 5,751,534 A | 5/1998 | DeBalko | |
| 5,776,737 A | 7/1998 | Dunn | |
| 5,786,142 A | 7/1998 | Renfrew et al. | |
| 5,789,168 A | 8/1998 | Leushner et al. | |
| 5,821,058 A | 10/1998 | Smith et al. | |
| 5,830,657 A | 11/1998 | Leushner et al. | |
| 5,834,189 A | 11/1998 | Stevens et al. | |
| 5,849,542 A | 12/1998 | Reeve et al. | |
| 5,853,979 A | 12/1998 | Green et al. | |
| 5,891,632 A | 4/1999 | Imai | |
| 5,916,747 A | 6/1999 | Gilchrist et al. | |
| 5,981,186 A | 11/1999 | Gabe et al. | |
| 6,005,663 A | 12/1999 | Waterhouse et al. | |
| 6,013,444 A | 1/2000 | Dau et al. | |
| 6,027,709 A | 2/2000 | Little et al. | |
| 6,068,737 A | 5/2000 | De Chamorro et al. | |
| 6,083,699 A | 7/2000 | Leushner et al. | |
| 6,195,449 B1 | 2/2001 | Bogden et al. | |
| 6,208,941 B1 | 3/2001 | Marks | |
| 6,303,303 B1 | 10/2001 | Green et al. | |
| 6,397,150 B1 * | 5/2002 | Izmailov | 702/20 |
| 6,404,907 B1 | 6/2002 | Gilchrist et al. | |
| 6,413,718 B1 | 7/2002 | Leushner et al. | |
| 6,428,955 B1 * | 8/2002 | Koster et al. | 435/6 |
| 6,485,625 B1 * | 11/2002 | Simpson et al. | 204/601 |
| 6,554,987 B1 | 4/2003 | Gilchrist et al. | |
| 6,716,394 B2 * | 4/2004 | Jensen et al. | 422/68.1 |
| 2002/0147548 A1 * | 10/2002 | Walther et al. | 702/20 |
| 2004/0072182 A1 * | 4/2004 | Lyamichev et al. | 435/6 |
| 2004/0117130 A1 * | 6/2004 | Denisov et al. | 702/20 |
| 2005/0042668 A1 * | 2/2005 | Perlin | 435/6 |

FOREIGN PATENT DOCUMENTS

| | | |
|---|---|---|
| EP | 0198403 | 10/1986 |
| EP | 0265293 | 4/1988 |
| EP | 0294524 | 12/1988 |
| EP | 0386859 | 9/1990 |
| EP | 0476712 | 3/1992 |
| EP | 0504943 | 9/1992 |
| EP | 0592060 | 4/1994 |
| EP | 0655506 | 5/1995 |
| GB | 2225139 | 5/1990 |
| WO | WO 8907149 | 8/1989 |
| WO | WO 9218650 | 10/1992 |
| WO | WO 9302212 | 2/1993 |
| WO | WO 9308305 | 4/1993 |
| WO | WO 9426894 | 11/1994 |
| WO | WO 9635810 | 11/1994 |
| WO | WO 9504140 | 2/1995 |
| WO | WO 9506756 | 3/1995 |
| WO | WO 9511961 | 5/1995 |
| WO | WO 9601008 | 1/1996 |
| WO | WO 9601909 | 1/1996 |
| WO | WO 9702488 | 1/1997 |
| WO | WO 9740184 | 10/1997 |
| WO | WO 9741259 | 11/1997 |
| WO | WO 9800708 | 1/1998 |
| WO | WO 9811258 | 3/1998 |
| WO | WO 9824930 | 6/1998 |
| WO | WO 9841650 | 9/1998 |
| WO | WO 0000637 | 1/2000 |
| WO | WO 0068410 | 11/2000 |

OTHER PUBLICATIONS

Arnot, et al., "Digital codes from hypervariable tandemly repeated DNA sequences in the *Plasmodium falciparum* circumsporozoite gene can genetically barcode isolates", *Molecular and Biochemical Parasitology* 61: 15-24 (1993).

Beebe, et al., "Incidence of *Neisseria gonorrhoeae* Isolates Negative by Syva Direct Fluorescent-Antibody Test but Positive by Gen-Probe Accuprobe Test in a Sexually Transmitted Disease Clinic Population", *Journal of Clinical Microbiology* 31(9):2535-2537 (Sep. 1993).

Bej, et al., "Detection of Coliform Bacteria and *Escherichia coli* by Multiplex Polymerase Chain Reaction: Comparison with Defined Substrate and Plating Methods for Water Quality Monitoring", *Applied and Environmental Microbiology* 57(8): 2429-2432 (Aug. 1991).

Bej et al., "Multiplex PCR amplification and immobilized capture probes for detection of bacterial pathogens and indicators in water", *Molecular Cellular Probes* 4: 353-365 (1990).

Bowling, et al., "Neighboring Nucleotide Interactions During DNA Sequencing Electrophoresis", *Nucleic Acids Research* 19: 3089-3097 (1991). (Abstract only.).

Carothers, et al., "Point Mutation Analysis in a Mammalian Gene: Rapid Preparation of Total RNA, PCR Amplification of cDNA, and *Taq* Sequencing by a Novel Method", *BioTechniques* 7(5):494-498 (May 1989).

Church, et al., "Genomic Sequencing", *Proc. Natl. Acad. Sci. USA* 81: 1991-1995 (1984).

Church, et al., "The Genomic Sequencing Technique", *Medical Genetics: Past, Present, Future*, pp. 17-21 (1985).

De Schryver, et al., "Epidemiology of sexually transmitted diseases: the global picture", *Bulletin of the World Health Organization* 68:639-654 (1990).

Dear, et al., "A sequence assembly and editing program for efficient management of large projects", *Nucleic Acids Research* 19(14): 3907-3911 (1991).

Deng, et al., "Simultaneous amplification and sequencing of genomic DNA (SAS): sequencing of 16S rRNA genes using total genomic DNA From *Butyrivibrio fibrisolvens*, and detection and genotyping of nonculturable mycoplasma-like organisms directly from total DNA isolated from infected plants", *Journal of Microbiological Methods* 17: 103-113 (1993).

Eisenstein, Barry I. M.D., "The Polymerase Chain Reaction: A New Method of Using Molecular Genetics for Medical Diagnosis", *The New England Journal of Medicine* 332: 178-183 (1990).

Ellison, et al., "Detection of Mutations and Polymorphisms Using Fluorescence-Based Dideoxy Fingerprinting (F-ddF)", *BioTechniques* 17(4): 742-753 (1994).

Erickson, Deborah, "Diagnosis by DNA: DNA-sequencing methods show clinical promise", *Scientific American.*, p. 116 (Oct. 1992).

Ewanowich, et al., "Major Outbreak of Pertussis in Northern Alberta, Canada: Analysis of Discrepant Direct Fluorescent-Antibody and Culture Results by Using Polymerase Chain Reaction Methodology", *Journal of Clinical Microbiology* 31(7): 1715-1725 (Jul. 1993).

Giddings, et al., "An adaptive, object oriented strategy for base calling in DNA sequence analysis", *Nucleic Acids Research* 21(19): 4530-4540 (1993).

Golden, III, et al., "Pattern Recognition for Automated DNA Sequencing: I. On-Line Signal Conditioning and Feature Extraction for Basecalling" (1991).

Gyllenstein, et al., "Generation of single-stranded DNA by polymerase chain reaction and its application to direct sequencing of the HLA-DQA locus", *Proc. Natl. Acad. Sci. USA* 85: 7652-7656 (1988).

Ingber, Lester, "Adaptive simulated annealing (ASA): Lessons learned", *Control and Cybernetics* (1995).

Ingber, Lester, "Lester Ingber's Code and Reprint Archive", http://www.ingber.com, 1-16 (May 1, 1997).

Ingber, Lester, "Simulated annealing: Practice versus theory", *Mathematical and Computer Modeling* 18: 29-57 (1993).

Ingber, Lester, "Very Fast Simulated Re-Annealing", *Mathematical and Computer Modeling* 12: 967-973 (1989).

Ingber, et al., "Genetic Algorithms and Very Fast Simulated Reannealing: A Comparison", *Mathematical and Computer Modeling* 16: 87-100 (1992).

Innis, et al., "DNA sequencing with *Themus aquaticus* DNA polymerase and direct sequencing of polymerse chain reaction-amplified DNA", *Proc. Natl. Acad. Sci. USA* 85: 9436-9440 (Dec. 1988).

Kaltaoboeck, et al., "Two-Step Polymerase Chain Reactions and Restriction Endonuclease Analyses Detect and Differentiate *ompA* DNA of *Chlamydia* spp.", *Journal of Clinical Microbiology* 30(5): 1098-1104 (May 1992).

Kambara, et al., "Real Time Automated Simultaneous Double-Stranded DNA Sequencing Using Two-Color Fluorophore Labeling", *BioTechnology* 9: 63-66 (Jul. 1991).

Koutny, et al., "Automated Image Analysis for Distortion Compensation in Sequencing Gel Electrophoresis", *Applied Spectroscopy* 46(1): 136-141 (1992).

Kretz, et al., "Cycle Sequencing", *PCR Methods and Applications* 3: S107-S112 (1994).

Krishnamani, et al., "Detection of a Novel Arginine Vasopressin Defect by Dideoxy Fingerprinting", *Journal of Clinical Endocrinology and Metabolism* 77: 596-598 (1993).

Landegre, et al., "DNA Diagnostics- Molecular Techniques and Automation", *Science* 242: 229-237 (Oct. 1988).

Langemeir, et al., "Application of Cycle Dideoxy Fingerprinting to Screening Heterogeneous Populations of the Equine Infectious Anemia Virus", *BioTechniques* 17(3): 484-490 (1994).

Lin, et al., "Characterization of Genetic Defects of Hemophilia A in Patients of Chinese Origin", *Genomics* 18: 496-504 (1993).

Mahony, et al., "Confirmatory Polymerase Chain Reaction Testing for *Chlamydia trachomatis* in First-Void Urine from Asymptomatic and Symptomatic Men", *Journal of Clinical Microbiology* 30(9): 2241-2245 (Sep. 1992).

Mahony, et al., "Multiplex PCR for Detection of *Chlamydia trachomatis* and *Neisseria gonorhoeae* in Genitourinary Specimens", *Journal Clinical Microbiology* 33(11): 3049-3053 (Nov. 1995).

Mason, Ivor J., "Rapid And Direct Sequencing Of DNA From Bacteriophage Plaques Using Sequential Linear and Asymmetric PCR", *BioTechniques* 12: 60-62 (Jan. 1992).

Maxam, et al., "A new method for sequencing DNA", *Proc. Natl. Acad. Sci. USA* 74(2): 560-564 (Feb. 1977).

Mayrand, et al., "The use of fluorescence detection and internal lane standards to size PCR products".

Miller, et al., "Chain Terminator Sequencing of Double-Stranded DNA with Built-In Error Correction", *General Atomics Preprint*, 1-48 (Jul. 1991).

Mullis, et al., "Specific Synthesis of DNA *in Vitro* via a Polymerase-Catalyzed Chain Reaction", *Meth. Enzymol.* 155: 335-350 (1987).

Murakawa, et al., "Direct Detection of HIV-1 RNA from AIDS and ARC Patient Samples", *DNA* 7(4): 287-295 (1988).

Murray, Vincent, "Improved double-stranded DNA sequencing using the linear polymerase chain reaction", *Nucleic Acids Research* 17(21): 8889 (1989).

Nuovo, G.J., "In situ PCR" in Dieffenback et al;, *PCR Primer: A Laboratory Manual*, pp. 235-248, Cold Spring Harbor Laboratory Press (1995).

Olesen, et al., "Chemiluminescent DNA Sequencing with Multiplex Labeling", *BioTechniques* 15(3): 480-485 (1993).

Plaschse, et al., "Doublex Sequencing in Molecular Diagnosis of Heriditary Diseases", *BioTechniques* 24, 838-841 (May 1998).

Rao, Venigalla B., "Direct Sequencing of Polymerase Chain Reaction-Amplified DNA", *Analytical Biochemistry* 216(1): 1-14 (Jan. 1994).

Reeve, et al., "A novel thermostable polymerase for DNA sequencing", *Nature* 376: 796-797 (Aug. 1995).

Reynolds, et al., *BioTechniques* 15: 462-467 (Mar. 1993).

Ruano, et al., "Automated Genomic Coupled Amplification and Sequencing (CAS) of the Mitochondrial D-Loop", Genomic Analysis Conference, Hilton Head, Fall 1994.

Ruano, et al., "Coupled amplification and sequencing of genomic DNA", *Proc. Natl. Acad. Sci. USA* 88: 2815-2819 (1991).

Ruano, et al., "Genotyping and haplotyping of polymorphisms directly from genomic DNA via coupled amplification and sequencing (CAS)", *Nucleic Acids Research* 19: 6877-6882 (1991).

Sanger, et al., "DNA sequencing with chain-terminating inhibitors", *Proc. Natl. Acad. Sci. USA* 74(12): 5463-5467 (Dec. 1977).

Sarkar, et al., "Dideoxy Fingerprinting (ddF): A Rapid and Efficient Screen for the Presence of Mutations", *Genomics* 13: 441-443 (1992).

Smith, et al., "Fluorescence detection in automated DNA sequence analysis", *Nature* 321:674-679 (1986).

Tabor, et al., "A single residue in DNA polymerases of the *Escherichia coli* DNA polymerase I family is critical for distinguishing between deoxy- and dideoxyribonucleotides", *Proc. Natl. Acad. Sci. USA* 92: 6339-6343 (Jul. 1995).

"Thermo Sequenase DNA polymerase", ThermoSequenase Product Insert (1995).

Tibbetts, et al., "Neural Networks for Automated Basecalling of Gel-based DNA Sequencing Ladders", pp. 219-229 (1987).

Warren, et al., "Comparative Evaluation of Detection Assays for *Chlamydia trachomatis*", *Journal of Clinical Microbiology* 31(6): 1663-1666 (Jun. 1993).

Way, et al., "Specific Detection of *Salmonella* spp. by Multiplex Polymerase Chain Reaction", *Applied and Environmental Microbiology* 59(5): 1473-1479 (May 1993).

Weiss, et al., "Enzymic Detection of Uracil in a Cloned and Sequenced Deoxyribonucleic Acid Segment", *Biochemistry* 22(19): 4501-4507 (1983).

Wiemann, et al., "Simultaneous On-Line DNA Sequencing on Both Strands With Two Fluorescent Dyes", *Analytical Biochemistry* 224: 117-121 (1995).

Xu, et al., "Multiplex DNA amplification and solid-phase direct sequencing for mutation analysis at the *hprt* locus in Chinese hamster cells", *Mutation Research* 288: 237-248 (1993).

\* cited by examiner

ELECTROPHORETIC TRACE SIMULATOR

This application claims the benefit under 35 USC § 119(e) of U.S. Provisional Application No. 60/332,471, filed Nov. 15, 2001, which is incorporated herein by reference in its entirety.

BACKGROUND OF THE INVENTION

This application relates to a method and an apparatus for simulation electrophoretic traces, particularly of the type generated by DNA sequencers. Electrophoretic traces generated by DNA sequencers routinely differ substantially from the theoretical pattern. The technique of automated DNA sequencing on denaturing polyacrylamide gels involves a complicated sequence of chemical, electrophoretic, and detection steps. At minimum, the following steps are required: (1) preparation of the sequencing template; (2) conduct of the sequencing reactions; (3) separation of the sequencing reaction products (DNA fragments) on a denaturing polyacrylamide gel; (4) excitation of the fluorescently-labeled DNA fragments, (5) detection of fluorescence emissions from the DNA fragments, and (6) analysis of the detector's data stream, to produce a called base-sequence. At each step in this path, distortions and errors can arise, which may lead to degradation of the collected data, or to biases or errors in the base-called sequence. It is challenging to identify, evaluate, and mitigate experimentally against all the potentially degradative or biasing influences on the determination of a DNA sequence. The common approach to these perturbations has been to manipulate the experimental data traces to adjust them to something that is closer to theoretical pattern. For example, commonly assigned U.S. Pat. Nos. 5,916,747 and 5,853,979, which are incorporated herein by reference, describe methodologies for normalization and alignment of DNA sequencing traces.

The goal of the present invention is to describe an electrophoretic trace simulation (ETS) method and apparatus that can help in this task.

SUMMARY OF THE INVENTION

The present invention takes an approach different from manipulation of an experimental data trace, and simulates the expected experimental data trace from an expected base sequence and assumed values for parameters such as system hardware, the type and quality of the gel, the sequencing chemistry and/or the sequencing template. The simulated trace prepared using the invention may be compared to an experimental trace having the same putative sequence (absent mutations which may be present in the experimental sample), and used to facilitate base calling. Since the simulated trace is determined with reference to an expected base sequence, each peak in the simulated trace is associated with a base position number in this sequence. Corresponding peaks in the experimental data trace are assigned the same base position number.

In many cases, the explicit determination of all four bases in a sequence is desired. In others, however, desired diagnostic information may be available from the explicit determination of the positions of less than all four base types. (See for example U.S. Pat. No. 5,834,189, which is incorporated herein by reference). Thus, the invention can be carried out to assess base positions in a data trace reflecting the positions of a single base or can be carried out on data trace(s) reflecting the positions of two, three or four bases.

DETAILED DESCRIPTION OF THE INVENTION

Figure 1:
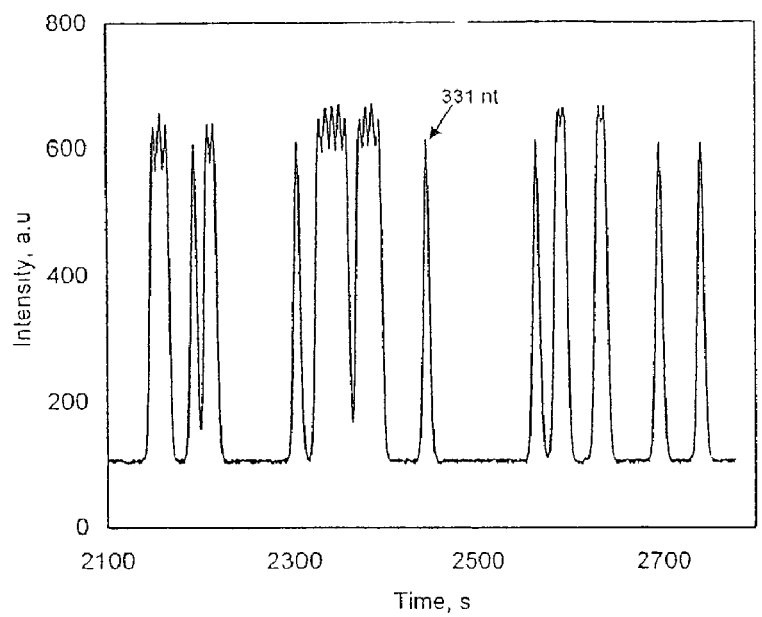
FIGS. 1A–D show calculated electrophoresis traces for different experimental conditions.
Figure 1:
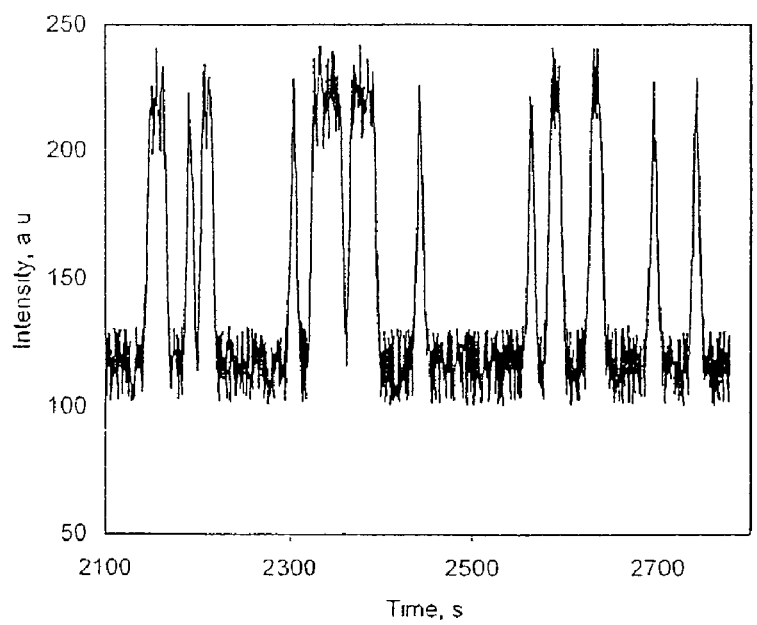
Figure 1:
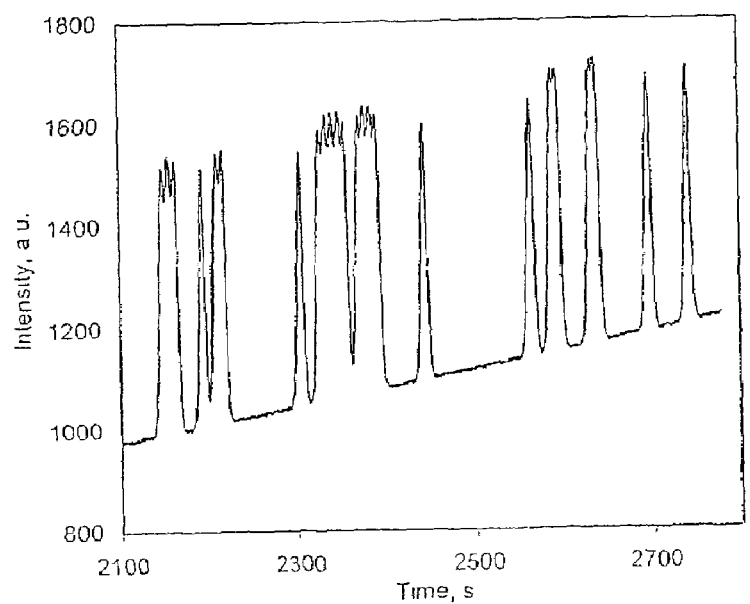
Figure 1:
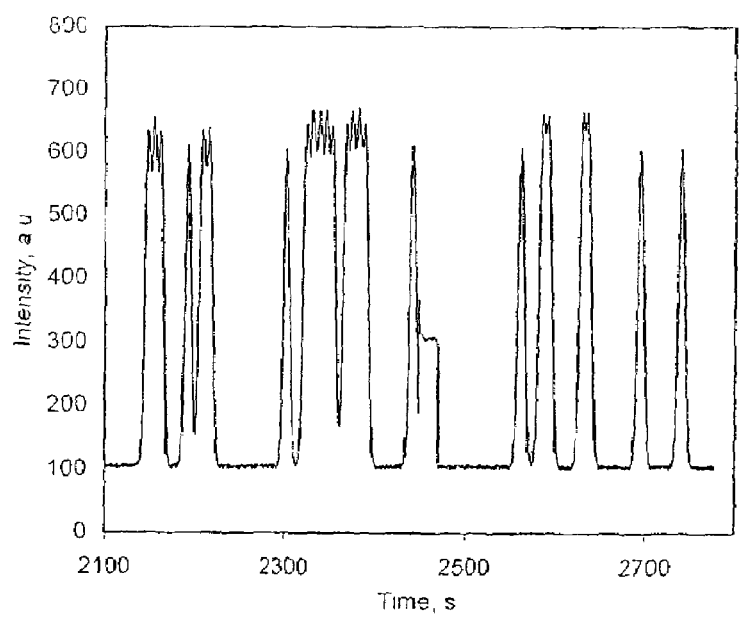

The present invention provides a method and apparatus for generation of a simulated electrophoretic trace. The Electrophoretic Trace Simulator (ETS) provides an algorithm for calculation of a set of electrophoresis traces, corresponding to the output of an automated fluorescent DNA sequencer (slab or capillary gels). This algorithm has several features, which will now be described.

1. Input File

As used in the specification and claims of this application, the term "input file" refers to a user-defined sequence of nucleotide bases, represented as a .txt or text file, that is used as the input to the trace simulator algorithm. This text represents a DNA sequence of interest, and consists of a string of letters A, C, G and T in the order corresponding to the sequence under consideration. A base number N is assigned to each letter in consecutive order starting from N=1 as a default. It is also possible for the user to pick some integer N>1 for a starting value. Simulation can be performed for a selected portion of the input file with user-defined start and end points.

In addition to the use of .txt file as an input, the program also allows experimentally recorded data files (output from automated DNA sequencers) to be used. These data files can be manipulated to induce distortions such as shift between traces, stretching, base line drift and jumps, cross talk or noise. Data files modified in such fashion can then be used to test the capabilities of base calling software.

2. Peak Intensity as a Function of Base Number

The peak intensity, $I_i(N)$, for each base (i=A, C, G or T) in the sequence is calculated as a function of base number N. The user can define the functional dependence of intensity on N by means of a formula. As a default, an exponential decay model is assumed. This is consistent with a mechanistic model of dideoxy-chain-termination DNA sequencing, in which there is a constant probability, at each template position, of chain-termination by incorporation of a dideoxy-nucleotide into the primer-extension product(s). In this model, the intensity distribution in a DNA sequencing ladder can be represented by an exponential-decay formula $$I_i(N) = I_{oi} \exp(-\beta_i N) \qquad (1)$$

where i=type of base (A, C, G, T), N=base number, $I_i(N)$ =intensity of ladder of type i as function of base number, $I_{0i}$=intensity of unextended primer within ladder of type i, and $\beta_i$=exponential decay parameter for the intensity of ladder of type i.

Because the chemical mechanism of the dideoxy-chain-termination reaction is the same for A-, C-, G- and T-reactions, the fundamental shape of the function $I_i(N)$ is expected to be the same for all DNA sequencing ladders. On the other hand, as the efficiency of the chain-termination reactions may vary, both the absolute intensity and decay rate may vary from one base type to another. The user has an option of choosing $I_{0i}$ and $\beta_i$ for each of the A-, G-, C- or T-terminated ladders. By choosing $\beta_i=0$, it is possible to simulate a trace with the peaks of equal intensity (independent of N).

An alternative built-in function for Ii (N) is given by the following formula:

$$I_i(N)=I_{0i}/(N-\alpha)^\gamma \quad (2)$$

where $\alpha$ and $\gamma$ are user-adjustable parameters which can be estimated from experimental data sets for different DNA sequencing reactions.

3. Peak Shape as a Function of Base Number

The broadening of bands during electrophoresis, and its dependence over base number, (with a consequent loss of resolution) is one of the key limiting factors in gel-based DNA sequencing methods. The Electrophoretic Trace Simulator takes this band-broadening effect into account. Various physical processes contribute to DNA band broadening during migration of DNA bands through an electrophoretic sequencing gel. The most important of these are: (1) the initial band width defined by loading or over-loading; (2) diffusion (thermal and electric field enhanced) during the electrophoresis; (3) non-homogeneities in the Joule heating or heat-exchange within the gel; (4) electro-osmotic flow (especially for capillary gels). It is usually assumed that, under a wide range of experimental conditions, the peaks in an electrophoresis run have a Gaussian shape. The width of the Gaussian function is affected by the above factors, which are considered to be independent. In the case of independent contributions to band-broadening, the square of total peak width (variance) can be expressed as the sum of squares of the individual factors (see for example, [1–4]).

For the peak corresponding to base number N, which migrates past a fixed detector as a function of time t, a Gaussian peak shape function is calculated using the following formula:

$$I_N(t) = \frac{I_{N0}}{\sigma_N \sqrt{2\pi}} \exp\left(\frac{-(t-t_N)^2}{2(\sigma_N)^2}\right) \quad (3)$$

where $I_N(t)$=fluorescent intensity at time t, within the peak corresponding to base number N; $I_{N0}$=intensity maximum of this peak, $\sigma_N$=width of peak (Gaussian standard deviation), and $t_N$=center of the peak. Note that the calculation is performed in the time domain. Note also that $\sigma_N$ is not a constant, but rather is a function of N.

The peak width function $\sigma_N$ depends not only on N, but also on various experimental conditions such as electric field strength, gel temperature, gel loading conditions, etc. One possible approach for specifying the $\sigma_N=f(N)$ function is to generate a theoretical formula, based on some accepted electrophoretic model. For example, theory suggests that a DNA sequencing gel should exhibit two regimes of separation (Ogston sieving and biased reptation), leading to different piecewise contributions to the=f(N) function. In the Ogston sieving regime (for DNA fragments less than about 200–300 nucleotides long), DNA molecules migrating through the gel exhibit a diffusional component of bandwidth that is predicted to have the following form: dif2(N) ~N–0.5 [5]. In contrast, in the biased reptation regime (for longer DNA fragments), the diffusional component of bandwidth is predicted to have the following form: dif2(N)~N –1.8–2 [2]. It should be noted that, if a theoretical model of diffusional peak broadening is used, then this model should also include a term for electric field dependence (see, for example [6]).

Another approach for specifying the $\sigma_N=f(N)$ function is to treat it as a polynomial, and then to fit the polynomial coefficients to an observed data set. Using this approach, the authors of [7] determined that, on a typical sequencing gel, $\sigma_N$ could be represented as a linear function of N over the 0–700 nucleotide range.

4. Peak Skew

Either the analytic or empirical approach for specifying the $\sigma_N=f(N)$ function can be used with the Electrophoretic Trace Simulator. Regardless of which approach is used, one additional effect should be taken into account. It is known from the literature that, under some experimental conditions, the peak shape is distorted and cannot be described by a pure Gaussian function. Rather, it is necessary to employ a skewed Gaussian function.

The underlying reasons for peak skew are numerous and varied. One factor that causes this type of distortion is a concentration overload. The peak shape in such a situation was studied for example by [8–10]. Another reason for peak skew is the fact that electrophoresis and diffusion are coupled, leading to a trailing edge effect [6]. A third reason may be non-homogeneity in the pore size distribution in the gels [11].

Three types of modified Gaussian functions are available for treating peak skew within the Electrophoretic Trace Simulator.

(1) The first is a combination of Gaussian and linear functions. For a peak with a leftwards skew (tail at the lagging edge), the left part of the peak is calculated is a weighted average of an increasing linear function and a Gaussian function. The right part of the peak is kept as a Gaussian. For the peak with a rightwards skew, the complementary approach is taken.

(2) The second method for treating peak distortion combines a Gaussian function with the function $f=b/(t-t_N)^c$. The constant b is a scaling factor, which in a combination with the power c allows a modification of the shoulder of the peak.

(3) In the third approach for treating peak distortion, a Gaussian function is used for both halves of the peak, but different peak widths are used for the left and right sides of the peak. This approach gives a smooth curve and considerable flexibility in peak characterization.

5. Spacing Between Peaks

In an automated fluorescent DNA sequencing run, the time required for each DNA band to travel from the well to the detector (at a fixed distance down the gel) is a characteristic function of the base number (N) and of the experimental run parameters. A number of different theoretical approaches have been proposed, for describing the electrophoretic migration of DNA molecules through a denaturing polyacrylamide gel (see e.g. [6] for review).

The Electrophoretic Trace Simulator treats the migration of DNA bands by introducing a time scale t, in place of a base number scale. This time scale is an analytic representation of the electrophoresis time as a function of base number. Examples of such functions for different experimental conditions and for different models of electrophoresis can be found in the literature (see [12, 13] for example).

If the range of DNA lengths under consideration can be definitely assigned to one of the migration mechanisms, then a theoretical model can be used for calculation of peak spacing. The other possibility is to empirically approximate the function t=t(N) with a polynomial as in [14]. Thus:

$$t(N) = t_0 + \sum_i a_i N^i \quad (4)$$

where $a_i$ are the polynomial coefficients, and i is the degree of the polynomial. The degree of the polynomial and the polynomial coefficients are found empirically, by using the least-squares method to fit the calculated curve to the experimental data. The same approach can be taken to simulate electrophoretic traces for experimental conditions that correspond to boundaries between different separation regimes, where it may be difficult to suggest an analytic description.

6. Background (or Baseline)

Typically the background (baseline) does not exhibit a significant variability or drift, and usually can be disregarded. However, background can become a significant limiting factor for electrophoretic traces that display low signal intensities. To address this situation, the Electrophoretic Trace Calculator has an option of adding background to a calculated trace, in the form of a polynomial function.

7. Noise

It is well known that noise may limit the quality of the information obtained from electrophoretic traces in automated DNA sequencing. The Electrophoretic Trace Simulator considers two separate cases, which represent different types of noise.

(1) First is instrument noise, which is always present in an experimental data set. The typical value of RMS (root mean square) noise in the VGI sequencer's data output stream is about 0.2–1% of the peak intensity. Such low values of instrument noise typically do not affect base calling. On the other hand, instrument noise may become important for traces that exhibit low signal intensities.

Instrument noise is modeled by the Electrophoretic Trace Simulator in the form of a sequence of random numbers in the range (0–1), which are multiplied by a coefficient representing maximum amplitude of the noise. This noise is added to the calculated trace.

(2) The other type of noise can be designated "chemical noise". Its origin is to be found in the sequencing chemistry, and typically is due to a combination of false priming and false termination events, catalyzed by the DNA polymerase enzyme. It is exacerbated when an impure sequencing template or impure primers are used.

Chemical noise may occasionally be severe enough, especially when combined with a low intensity of the true sequence, to produce base-calling errors. A pure simulation of chemical noise is difficult to describe analytically, with the exception of a specific false priming event, for which the sequence producing the "chemical noise" might be known. Such a case can be modeled by specifying a text file corresponding to the distorting sequence, calculating the resultant electrophoretic trace, and adding it to the trace from the original sequence under simulation. Chemical noise that is due to random priming or termination events, and thus unpredictable, could be treated by using, as input to the Electrophoretic Trace Simulator, a random sequence, having an intensity distribution set at some fraction, say 10%, of the primary sequence. The primary sequence trace and the trace due to the chemical noise would then be added together point by point.

8. Cross-Talk

In the majority of multicolor automated DNA sequencers, the emission spectra of different fluorescent dyes display a significant amount of spectral overlap. Therefore, the light emitted by one fluorophore is simultaneously collected by several detection channels. This dictates a necessity for cross-talk compensation. Obviously, if the coefficients in the crosstalk compensation matrix are incorrect, then this will lead to under-compensation or over-compensation, during the correction process. Low levels of residual cross-talk are treated by the base-calling software as small variations of the baseline, and can be suppressed. However, above a certain level of relative intensity, cross-talk under-compensation may lead to errors in base calling.

The Electrophoretic Trace Simulator allows the calculation of traces with over-(or under-) compensation, with an adjustable amplitude. This allows one to estimate the impact on base-calling accuracy.

To demonstrate the use of the ETS in accordance with the invention, experimental data sets were generated by cycle-sequencing of an M13mp18(+) template with a Cy5.0- or Cy5.5-labeled M13 universal (−21) primer. All reagents were obtained from Visible Genetics cycle sequencing kits (part # VG 30001), and the sequencing reactions were run according to the kit package insert. The sequencing reactions were analyzed on Visible Genetics Long Read Tower electrophoresis platform, using MicroCel 500 gels or MicroCel 700 gels (195 mm or 255 mm well-detector distance, respectively) under the following run conditions: plate temperature T=54° C. for MicroCel 500 gels and T=60° C. for MicroCel 700 gels, field strength E=100 V/cm, laser power=1.5 mW per lane, data sampling period=0.5 sec for MicroCel 500 gels and 1 sec for MicroCel 700 gels. Sequencing data were collected and analyzed using the Visible Genetics Gene Objects Software, version 3.1.

Figure 7:
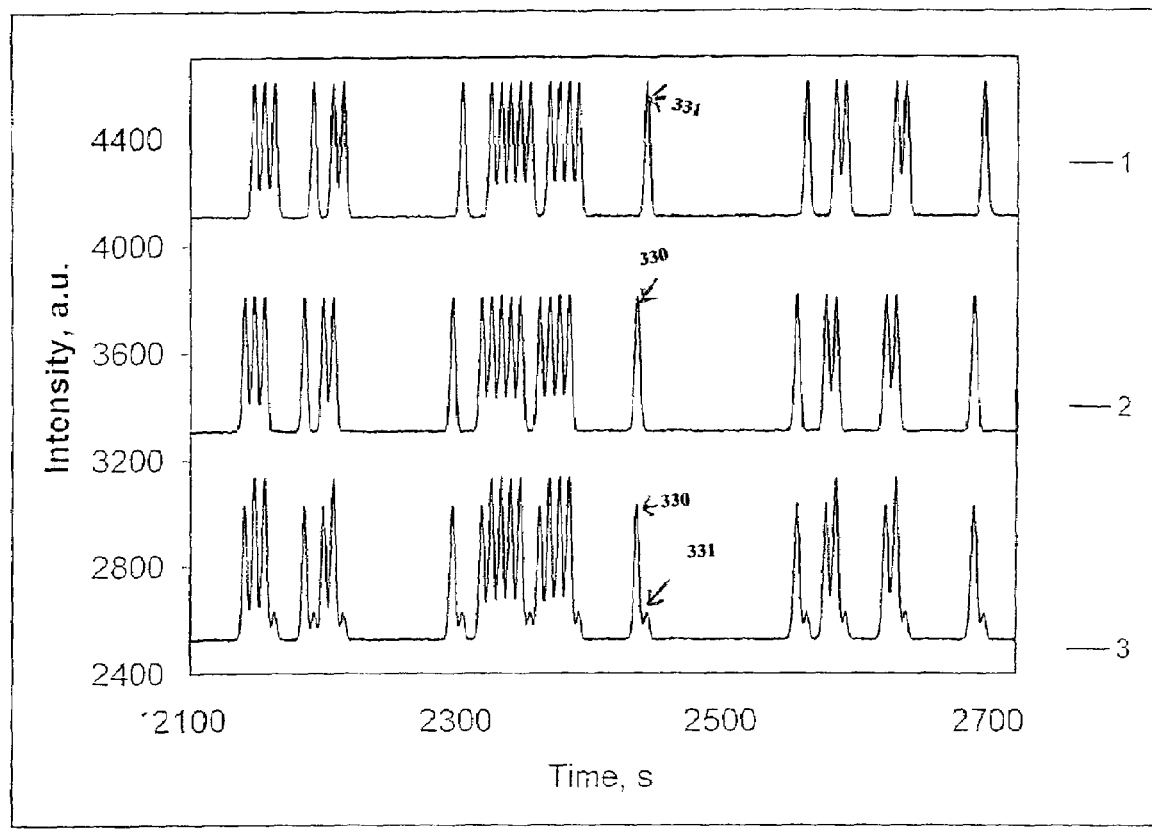
FIG. 7 shows the effect of a defective primer.

As a control, we first calculated traces for a normal run of M13mp18 sequence. A portion of this calculation, for the region of the T-track around the diagnostic "5-0-4" multiplet, is shown in FIG. 1A. The peak of absolute length 331 nucleotides is indicated, for reference. A larger portion of this same calculated trace is shown in FIG. 7, Curve 1.

Having established that the Electrophoretic Trace Simulator could produce acceptable control traces, we next used the program to model various situations in which instrument factors were expected to limit performance.

FIG. 1B shows the results of a trace calculation for a low Signal/Noise ratio. The signal is decreased by a factor of ~3x, and the noise is increased by a factor of ~2x relative to the trace shown in FIG. 1A. The diagnostic "5-0-4" peak, between nucleotide positions 312–331 in the M13mp18 T-ladder is shown.

FIG. 1C shows a calculated trace in which a linear baseline drift is introduced. The drift has an approximate magnitude of +3 counts/10 sec. In practice, such an effect can be observed during warm-up of the instrument, or because of instability in the amplifier output.

FIG. 1D shows a calculated trace in which a baseline jump of ~200 counts occurs, shortly after the T-331 peak. In practice, this could be caused by a sudden increase in scattering of excitation laser light, due to the appearance of a bubble in the gel, or a dust particle in the optical path. It could also be caused by an instability in the instrument electronics.

Figure 2:
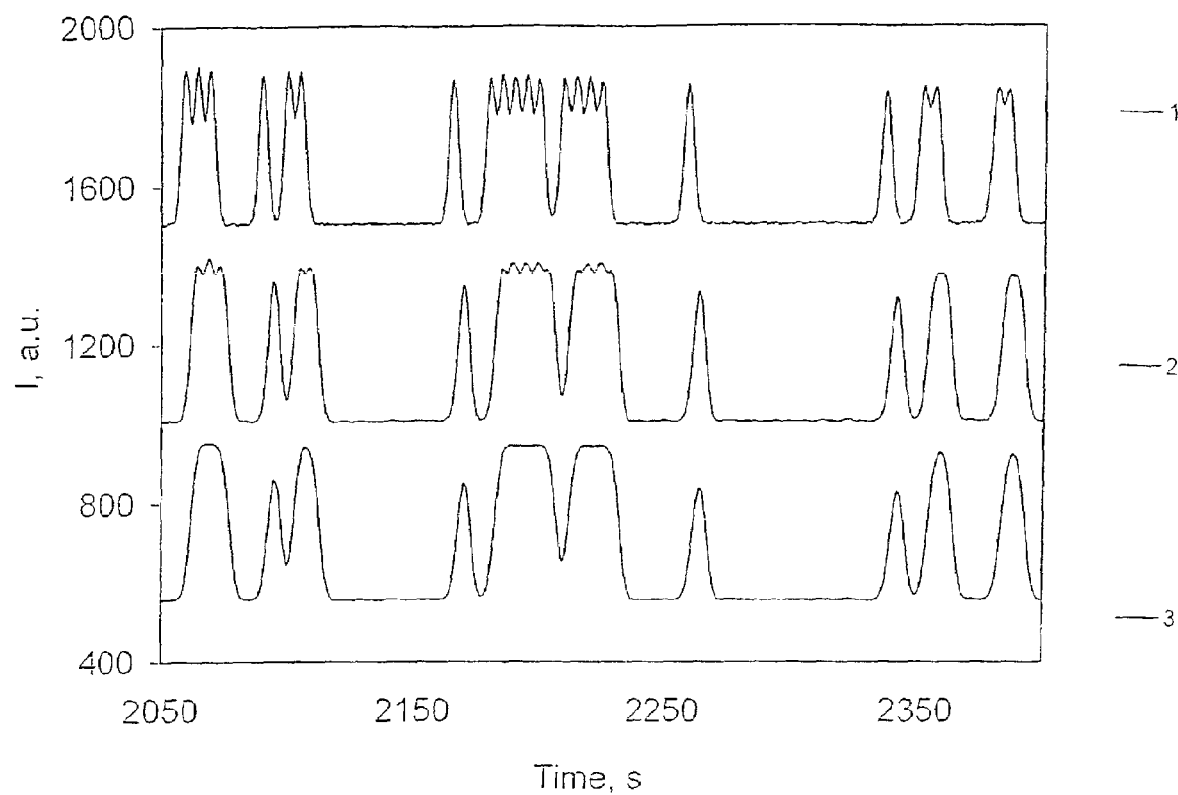
FIG. 2 shows the effect of defocused optics in a simulated electrophoresis trace.

The optical path of an automated DNA sequencer must be maintained within tight specifications. If this is not done, then a "defocusing" of the laser beam will effectively occur, leading to illumination of the larger gel area and as a result causing a loss of resolution and thus limiting the maximal read length in a sequencing assay. Other types of defocusing (in the light collection path, for example) can also occur depending on the sequencer design leading to the same consequences. FIG. 2 presents the results of a simple trace calculation, in which optical defocusing is simulated by averaging adjacent data points in the trace. Laser spot diameters of 40, 80, and 200 μm diameter are simulated in Curves 1, 2, 3 respectively. Averaging was performed in the second two simulations on 2 and 5 points respectively. A more sophisticated approach to this problem would involve convoluting the Gaussian peak function (eq. 3) with a blurring or smearing function, that could be computed from an optical analysis [15].

The Visible Genetics sequencing platform employs two dyes (Cy5 and Cy5.5) which display significant overlap in their fluorescence emission spectra. The coefficient that describes cross-talk from the Cy5 channel to the Cy5.5 channel has a value of about 0.5, and the coefficient describing cross-talk from the Cy5.5 channel to the Cy5 channel has a value of about 0.1. The disparity between the two cross-talk coefficients is the result of the asymmetric shapes of the emission spectra of the two dyes. Four-color sequencers also experience a relatively high level of cross-talk. Appropriate compensation probably is essential even for a low level of cross-talk.

Figure 3:
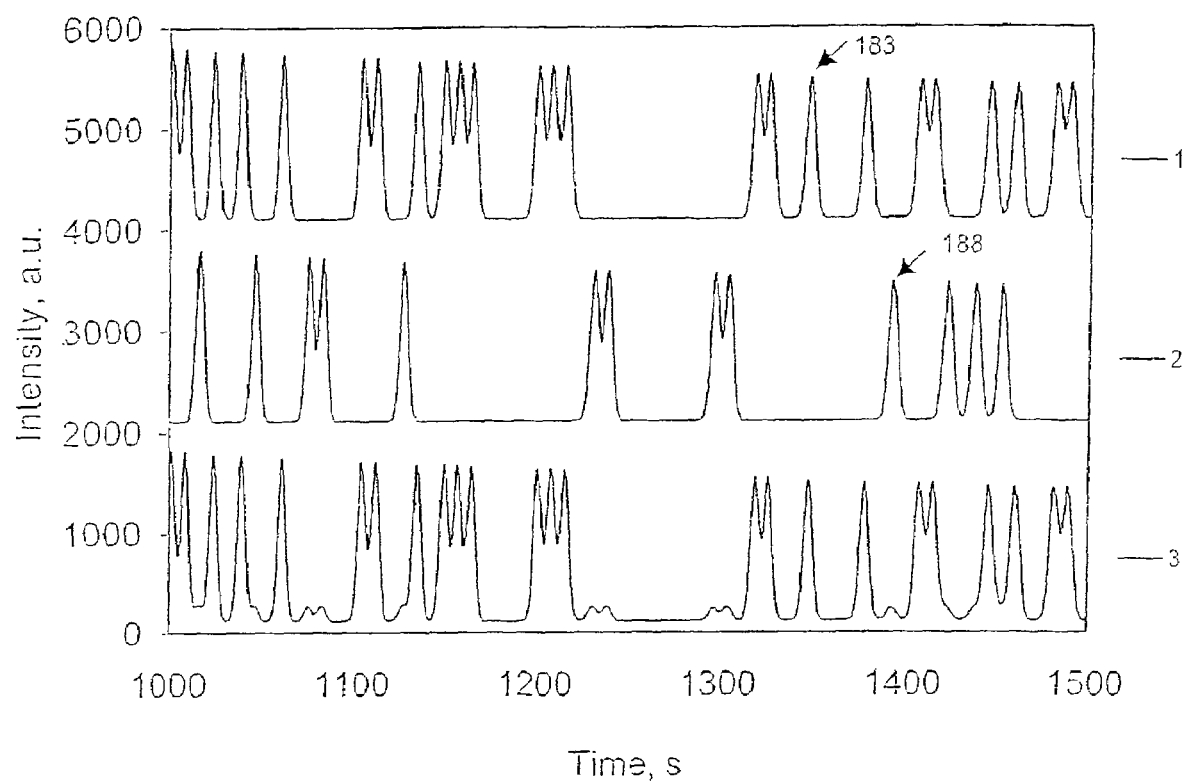
FIG. 3 shows the effect of residual crosstalk in a simulated electrophoresis trace.
Figure 4:
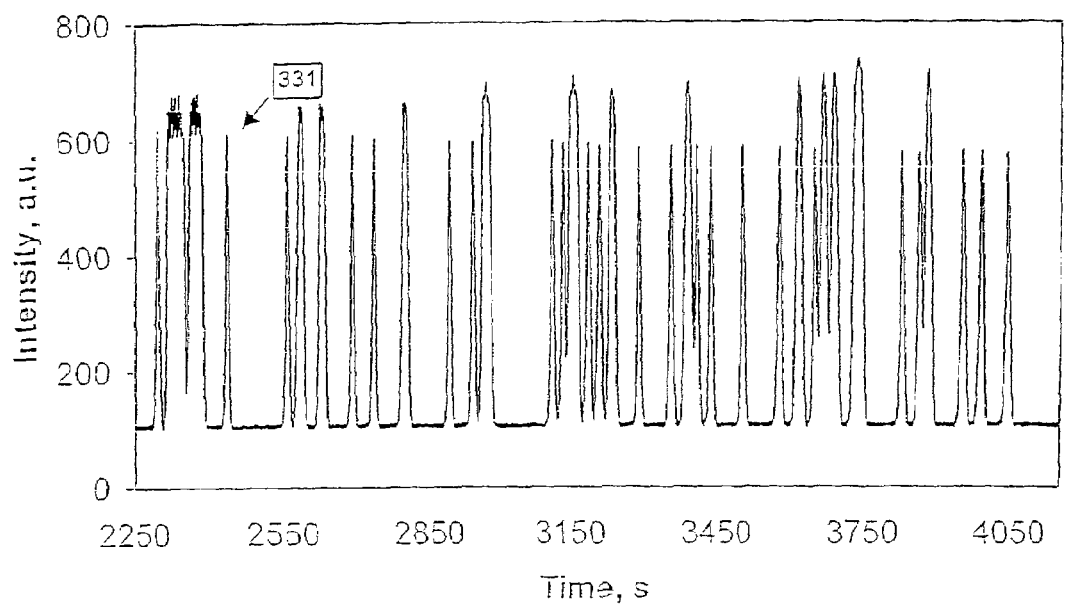
FIGS. 4A and B show the effect of high electric field strength on separation in the "biased reptation" regime.
Figure 4:
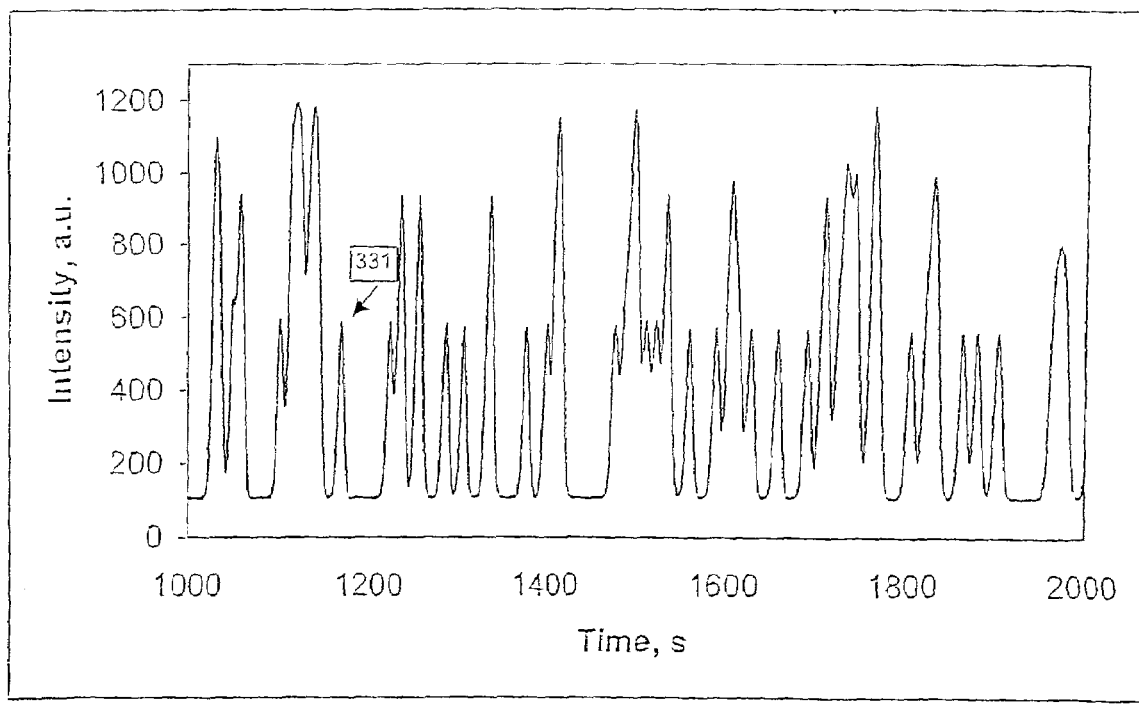

If the cross-talk is under-compensated, then false peaks will appear in each channel, which are due to cross-talk from true peaks in the other channel. This problem can become critical when the signal strength in the two channels is unequal. In such a case, cross-talk from peaks in the strong channel can produce apparent (but false) peaks in the weak channel, which may erroneously be base-called. FIG. 3 shows the calculated traces for a situation in which the cross-talk is under-compensated. Curves 1 and 2 in this Figure show the traces calculated with no cross-talk for the A-track and C-track respectively, around position 160–190 in the M13mp18 sequence. Curve 3 shows a situation in which approximately 10% of the intensity of the C-track is cross-registered in the A channel. The cross-registered peaks, although small, are of positive intensity, and thus could conceivably be mistaken for real peaks by the base-calling software. An over-compensation leads to negative peaks, which are not likely to be selected by the base-calling software. 3.3.1 Electric Field Effects, in the Biased Reptation Regime of Separation Many investigators have observed that the separation of DNA fragments in the "biased reptation" regime is dependent upon electric field strength (see e.g. [6, 16]. The greater the electric field strength, the poorer the separation of large fragments. The Electrophoretic Trace Simulator was used to model this effect. As a very simple first approximation, an inverse dependence on field strength was used in the equation for peak spacing, while no field-strength dependence was used in the equation for peak width. (We note that other models, of greater sophistication, could easily be implemented with the Electrophoretic Trace Simulator). Calculations for two field strengths (E2 2 E1) were performed. A region around the diagnostic "5–0–4" multiplet is shown in FIGS. 4A and B. Two effects are evident. (1) The electrophoretic velocity of peaks is increased in proportion to the increase in field strength. (2) Because adjacent peaks are closer together at high field strength, the resolution is decreased.

In DNA sequencers that employ less than 4 colors per lane, information about the linear order of the four bases (A, C, G, T) in a sequence is obtained from co-analysis of electrophoretic traces from two or more gel lanes. These lanes are physically separated, and the samples therein may electrophorese with different velocities due to loading delays between lanes, nonhomogeneities of the gel or electric field, or temperature gradients. Such differences in electrophoretic velocity will be translated into a shift (in time scale) of one trace relative to another, and perhaps also into a stretch (expansion or compression of one trace, relative to another). Base calling algorithms usually compensate for these effects, if not too severe. The Electrophoretic Trace Simulator can help to determine the limits of trace stretching and/or shifting which can be handled by the base-calling software. An example of lane misalignment will be discussed further below, in the section entitled "3.6 Special Cases".

Figure 5:
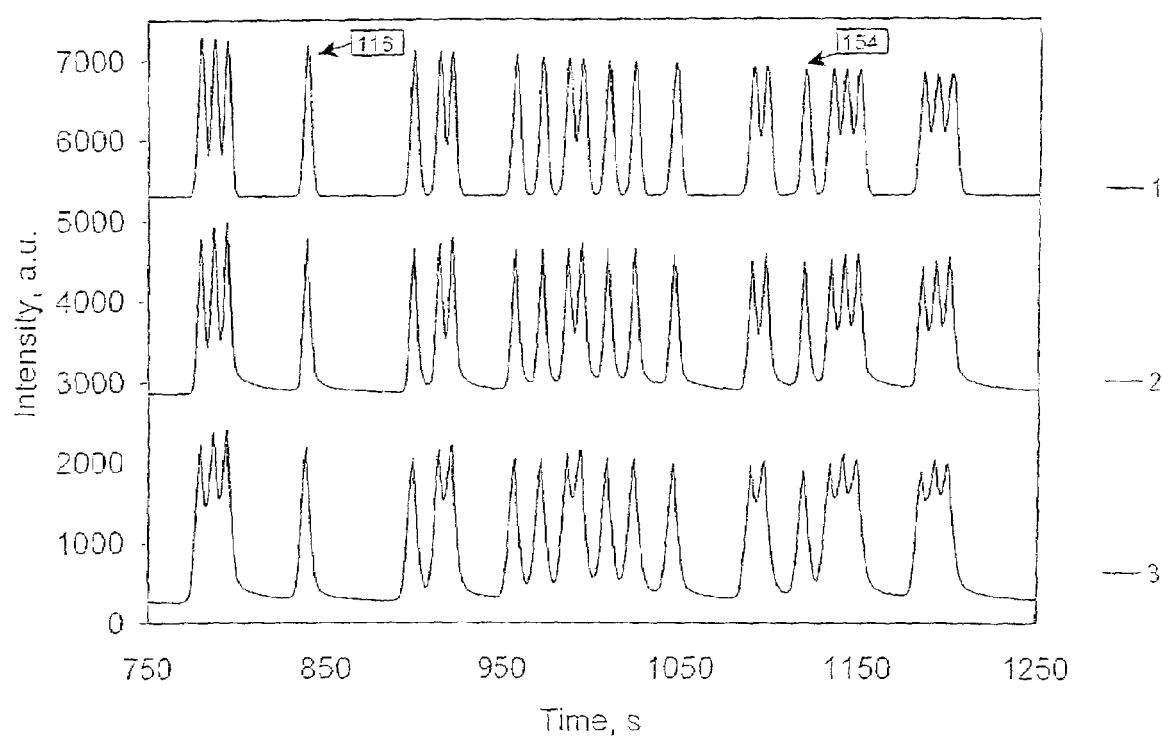
FIG. 5 shows a simulated electrophoresis trace with peak shape distortion.

As discussed above, it is often the case that bands in a sequencing gel are not perfectly Gaussian, but rather are distorted in one way or another. This case can be handled by the Electrophoretic Trace Simulator. An example is shown in FIG. 5. A portion of the M13mp18 A-track is shown, around positions 116–154. Curve 1 was generated by a control calculation, in which all peaks were purely Gaussian. In Curve 2, a right-hand skew has been added to each peak, which causes a slight loss of resolution. In Curve 3, an additional distortion (a 2-fold increase of peak width) has been added, which in combination with the skew produces a significant loss of resolution.

The chemistry of automated fluorescent DNA sequencing is relatively complex, and there are many opportunities where chemical raw materials, intermediates, and reaction steps may be non-optimal. The Electrophoretic Trace Simulator can be used to help troubleshoot problems encountered in the sequencing chemistry, as two examples will illustrate.

Figure 6:
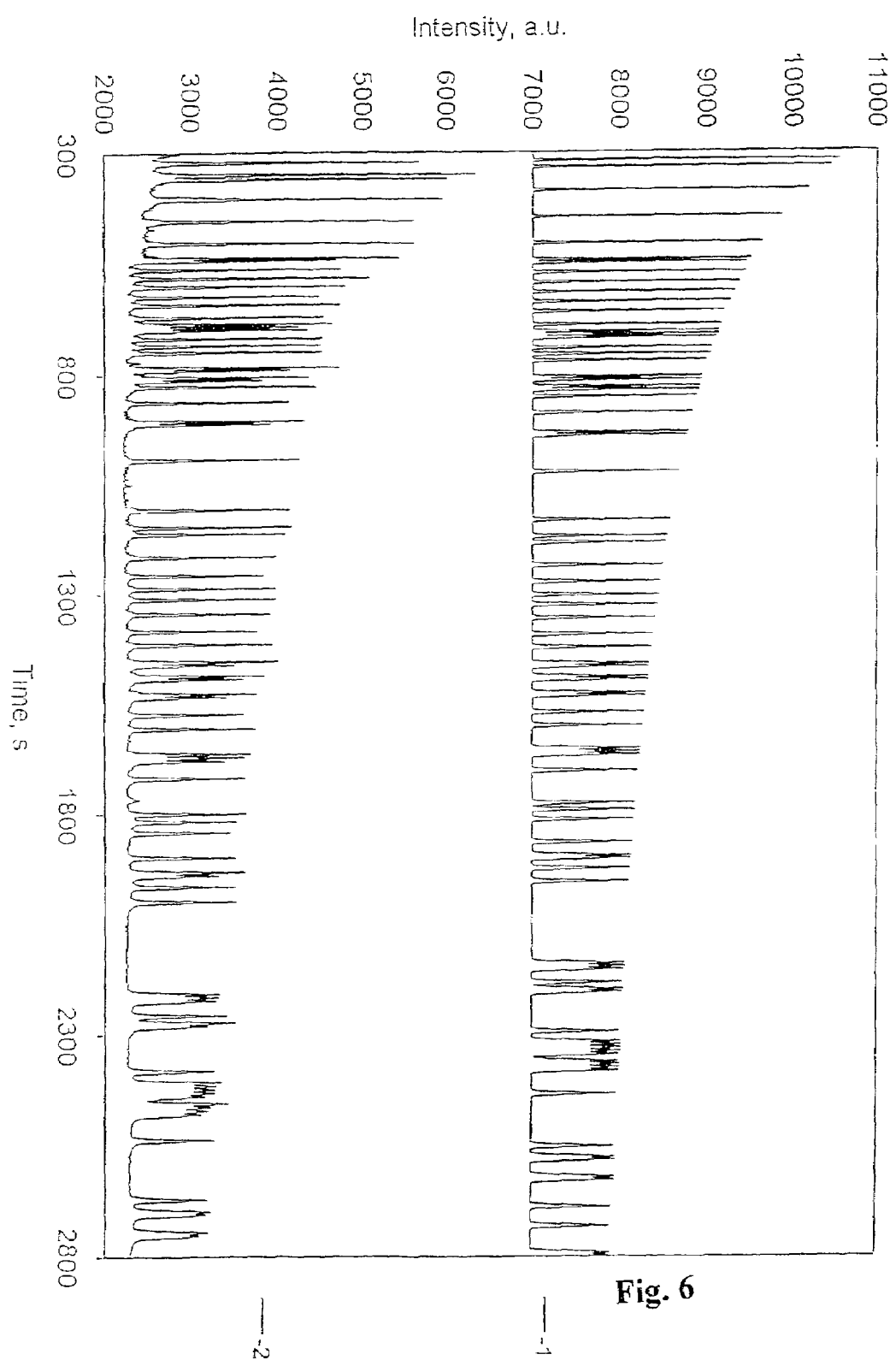
FIG. 6 shows exponential decay of signal intensity as a function of base number.

In dideoxy-chain-termination DNA sequencing, there is a constant probability, at each template position, of terminating the primer-extension product (nascent sequencing ladder), by incorporating a dideoxy-nucleotide into the growing DNA chain. This mechanism leads to the prediction of an an exponential decay of peak intensity, as a function of base number (N). The Electrophoretic Trace Simulator was used to model this situation. The intensity distribution in a sequencing ladder wase represented by an exponential decay, as given by Eq. (1). FIGS. 6A and B compares the results of simulation (FIG. 6A) with an actual experimental observation of the T-track of M13mp18 (FIG. 6B).

The Electrophoretic Trace Simulator can also be used within a risk analysis framework, to explore the consequences of possible defects in the manufacture of a genotyping kit. This simulation considers the possibility that, during the stepwise synthesis of a primer using phosphoramidite technology, only the first (m−1) synthesis cycles are completed with high efficiency. This would produce a situation in which a truncated primer, (m−1) nucleotides long and missing its 5'-terminal nucleotide, was a minor contaminant of the desired final primer (m nucleotides long). If a subsequent primer purification step was not performed, or was inadequate, then a mixture of two primers (of lengths m and m−1) would result.

If this mixture of primers was then used for sequencing, e.g. with dye-terminators, then a mixture of two sequences would result. The sequence generated by the (m−1)-long primer (FIG. 7, Curve 2) would be offset by −1 nucleotide position, relative to the sequence from the full-length primer (FIG. 7, Curve 1). Accordingly, it is predicted that, if sequencing is performed with such a mixture of primers, then the principal sequence will be contaminated by a "ghost sequence" that is offset by −1 nucleotide position FIG. 7, Curve 3 shows a predicted electrophorestic trace for sequencing reaction in which 10% of primer has length (m−1) and 90% of primer has length m.

Figure 8:
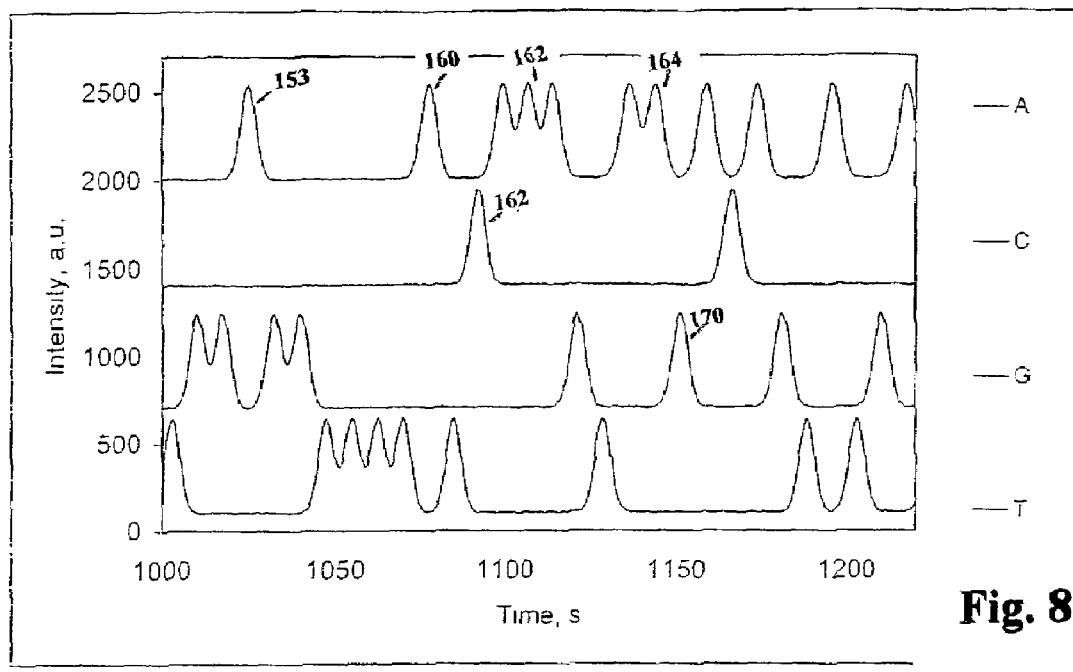
FIGS. 8A–C show simulation of the effect of sample contamination.
Figure 8:
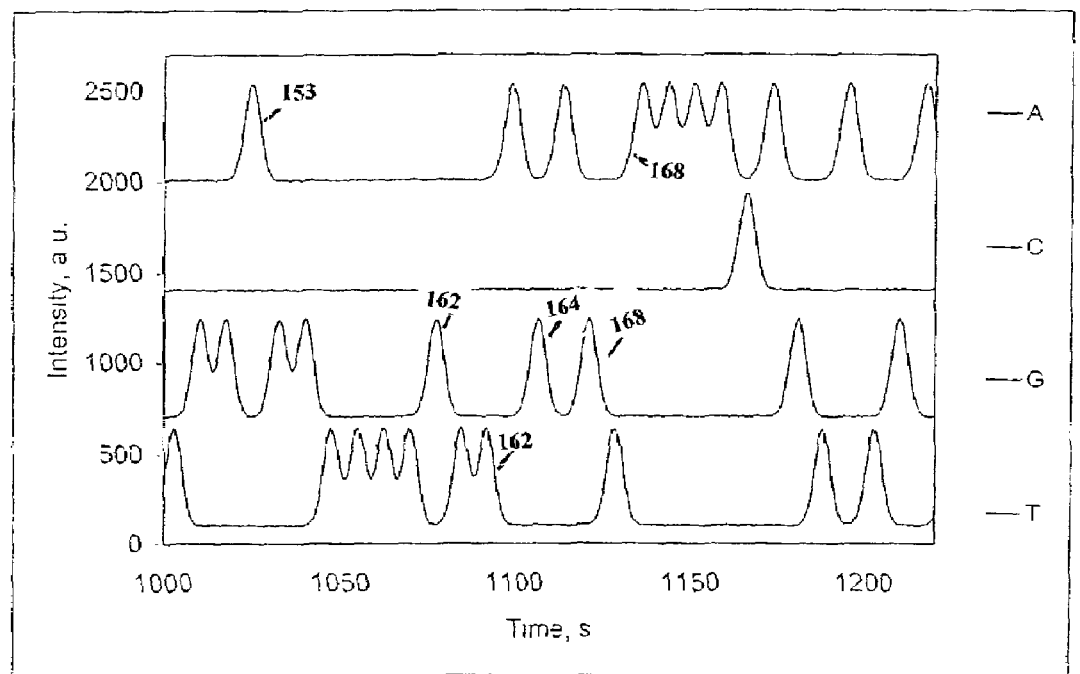
Figure 8:
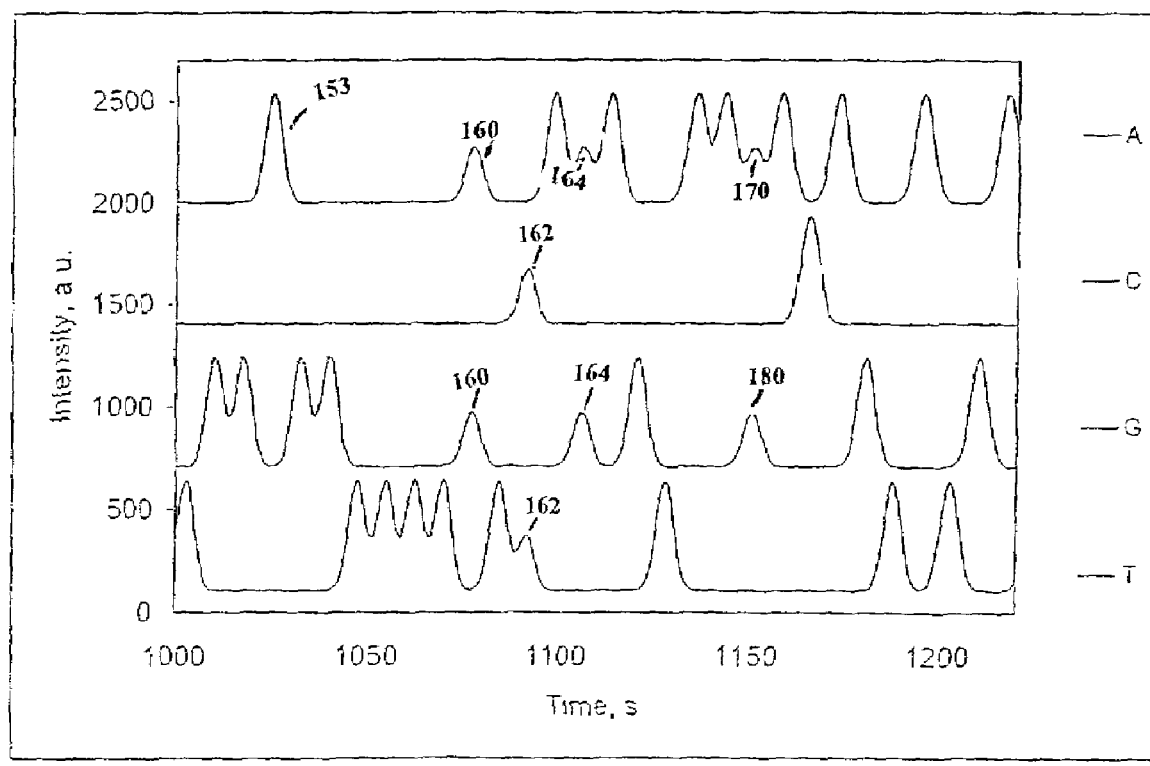

The Electrophoretic Trace Simulator can also be used within a risk analysis framework, to explore the consequences of a common problem in the use of a genotyping kit. In a field setting, it is essential to be able to detect cross-contamination of patient samples. The Electrophoretic Trace Simulator can be used to model the effects of mixing together two related (but non-identical) templates. FIG. 8A shows a set of four traces (A, C, G, T) that are computed over nucleotide positions 150–180 of the protease gene of a B-subtype HIV-1 sequence (GenBank # HIVHXB2CG). FIG. 8B shows a set of traces for this same region, computed for an F-subtype HIV-1 sequence (GenBank # AY010409). In FIG. 8C, the two sequences have been mixed together in a 1:1 ratio (as might be expected to occur for a case of sample contamination). At some of the positions (e.g. #153), there is no change. However, at other positions (e.g. #160) a mixture of two bases (A, G) is observed.

Figure 9:
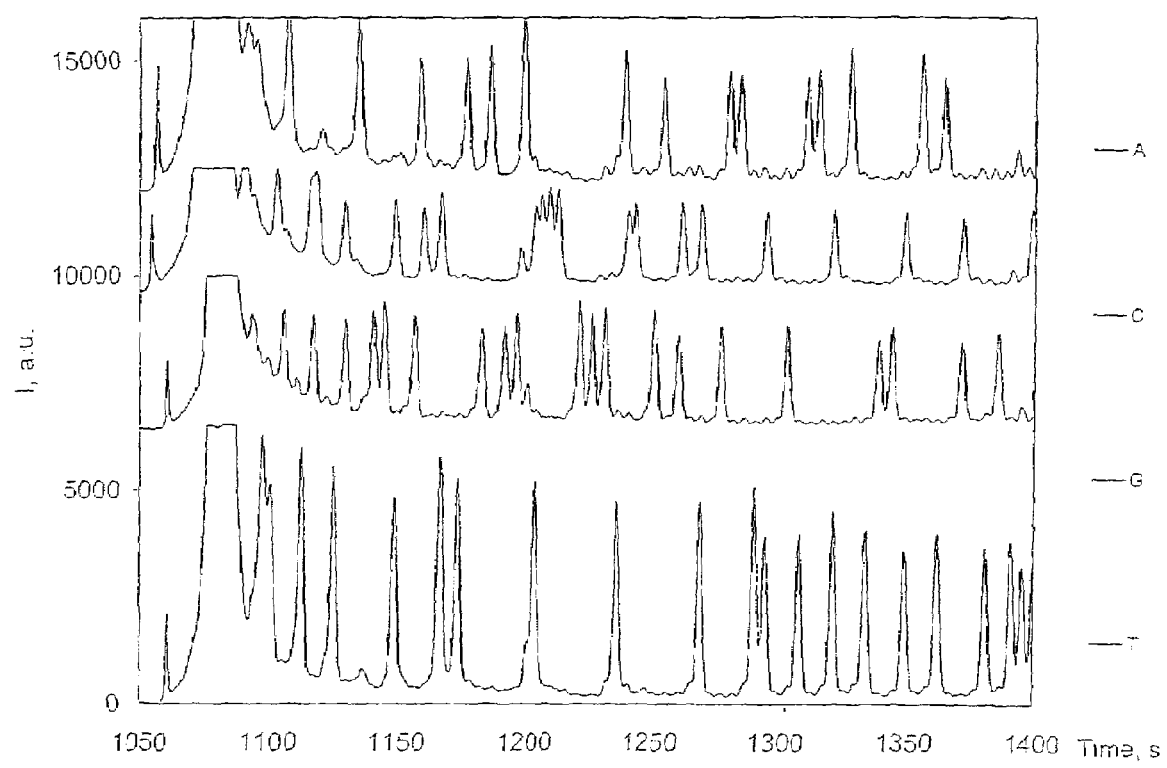
FIGS. 9A and B show the use of the electrophoretic trace simulator to add distortions or nosie to experimental data traces.
Figure 9:
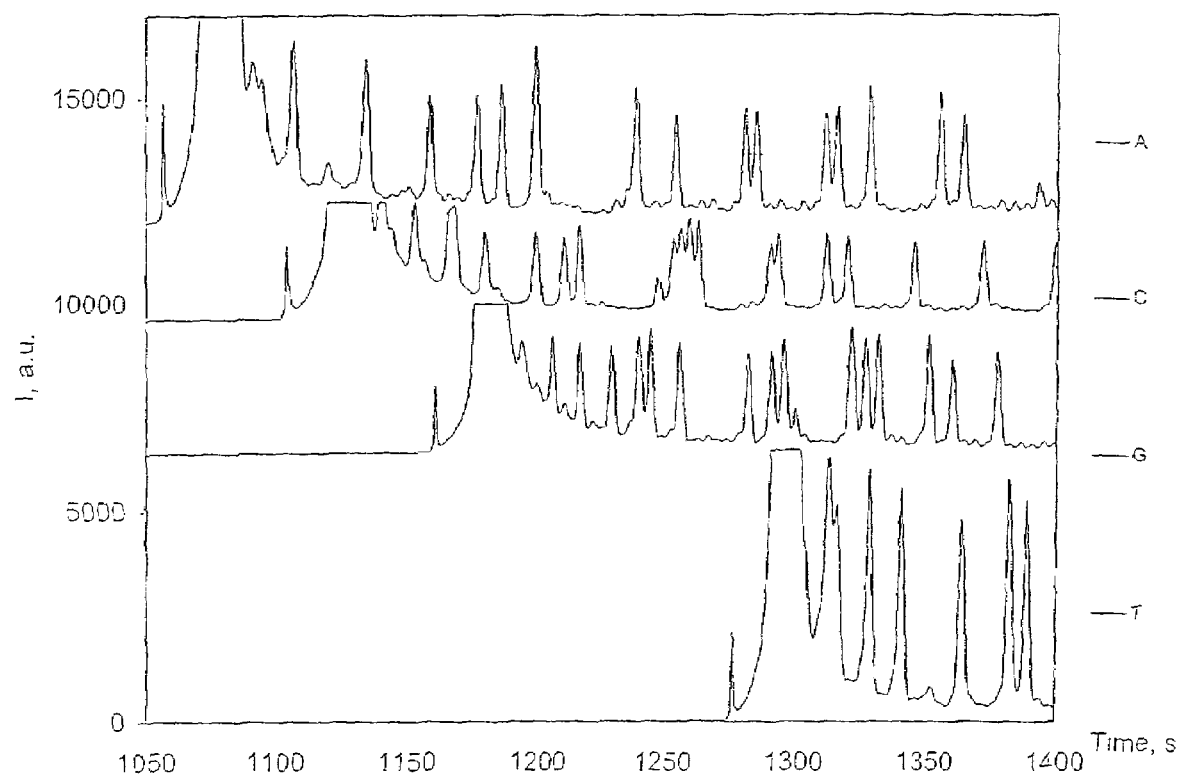

Electrophoretic traces may, in some cases, be too complex to simulate accurately. It may still be important to study the influence of various experimental conditions on them. For example, it would be useful to have the ability to introduce a known distortion into an experimentally recorded trace, and then to observe the effect of this distortion on subsequent base-calling. In order to have this capability, a function is incorporated into the Electrophoretic Trace Simulator, which allows the input of a data file typical for the output of the DNA sequencer comprising a set of data points (fluorescent intensity at each of a series of discrete time points). In this case, an experimental trace (in all its complexity) is used as a starting point, and is modified by adding special features of interest (residual cross-talk, baseline jumps, excessive instrument noise, etc.) This approach conveniently removes the necessity of generating chemical noise, for example, or other features by a theoretical model, which may be simplistic or flawed. A sample calculation of this type is shown in FIG. 9. In Panel A, a portion of an experimentally recorded electrophoretic trace from Cy5.5-labeled M13mp18 sequence is shown, from the primer peak to position ~100. The traces (A, C, G, T) are well-aligned and relatively noise-free. Panel B shows the effect of using the Electrophoretic Trace Simulator to introduce time-delays of 60, 60, and 120 see between adjacent traces. In addition, signal intensity was decreased and instrument noise was added to the C-trace. Thus, with the Electrophoretic Trace Simulator, it is straightforward to investigate the cumulative effects of adding different types of noise or distortion to a pre-existing electropherogram.

The Electrophoretic Trace Simulator (ETS) was used to calculate sets of electrophoresis traces that correspond to outputs from an automated fluorescent DNA sequencer. A user-defined sequence of bases (.txt file) serves as input for such calculations. The ETS employs user-adjustable functions for the following critical parameters of a DNA sequencing electropherogram: peak shape, peak spacing, dependence of peak intensity on base number, background, noise, and cross talk correction. It was shown that the Electrophoretic Trace Simulator can be used to model or predict the behavior of a DNA sequencing system, taking into account effects at the levels of: (1) the system hardware, (2) the electrophoretic gel, (3) the sequencing chemistry, and (4) the sequencing template.

In view of the foregoing, a first aspect of the invention is a method for creating a simulated electrophoretic trace. The method comprises the steps of obtaining an input file providing a base sequence comprising a string of letters (A, C, G and/or T) in an order corresponding to the input base sequence. These letters correspond to peaks, and are presumed in the initial data set to have equal spacing, equal peak heights (intensities) and equal widths. This data file of the input base sequence is then modified using one or more, and preferably a plurality of functions to take into account perturbations associated with (1) changes in peak intensity as a function of base number; (2) peak shape as a function of base number; (3) peak skew; (4) spacing between peaks; (5) background; (6) noise; (7) spectral cross-talk; (8) instrumental effects and (9) gel electrophoresis effects. It is not required to use all of the these functions to arrive at a suitable simulated electrophoretic trace. Where, for example, the length of the sequence is short, changes to peak intensity, or to peak shape may be minimal between the starting and ending base, making use of these functions unnecessary. Similarly, functions addressing instrumental effects and gel electrophoresis effects may have multiple components of which only some may be relevant for a given instrumental system or gel type. Appropriate functions for instrumental effects and gel electrophoresis effects can be determined by reverse calculation from sequencing runs performed under a set of standard conditions (for the instruments and gels being used) using reference standards of known sequence.

The method of the invention may be practiced using an apparatus in accordance with the invention. The apparatus comprises a programmed computer processor, for example a personal computer using any of several standard operating systems (Windows, Unix, Linux and the like) connected for communication to a storage device having stored thereon a stored set of program instructions for carrying out the method. Input devices such as keyboards, pointing devices, wired or wireless network connections, voice-recognizing audio-input systems, or movable storage media (for example diskettes) may be used to acquire parameter values which are used for processing the input sequence into a simulated electrophoresis trace. A video display may be provided as part of the apparatus to enhance the parameter input interface and display the results. The apparatus may be a dedicated apparatus which performs no other DNA sequencing-related function, or it may be a combination apparatus in which comparison of the simulated electrophoresis trace with an experimental data trace is performed to achieve analysis of a sample.

REFERENCES

The following references referred to herein are each incorporated herein by reference in their entirety.

[1] Giddings, J. C., Dynamics of Chromatography, Marcel Dekker, New York, 1965.
[2] Brahmasandra, S. N., Burke, D. T., Mastragelo, C. H., Bums, M. A., Electrophoresis 2001, 22, 1046–1062.
[3] Heller, C., Electrophoresis 1999, 20, 1978–1986.
[4] Kenndler, E., in: Khaledi, M. G. (Ed.), High-Performance Capillary Electrophoresis. Theory, Techniques and Applications, John Wiley & Sons, Inc., New York, 1998, pp. 25–76.
[5] Slater, G. W., Guo, H. L., Electrophoresis 1995, 16, 11–15.
[6] Slater, G. W., in: Heller, C. (Ed.), Analysis of Nucleic Acids by Capillary Electrophoresis, Vieweg Verlagsgesellschaft, Weisbaden 1997, pp. 24–66.
[7] Djouadi, Z., Bottani, S., Duval, M.-A., Siebert, R., Tricoire H., Valentin, L., Electrophoresis 2001, 22, 3527–3532.
[8] Mikkers, F. E. P., Everaerts, F. M., Verheggen, Th. P. E. M., J. Chromatogr. 1979, 169, 1.
[9] Thornann, W., Electrophoresis 1983, 4, 383.
[10] Pope, H., Anal. Chem. 1992, 64, 1908.
[11] Yager, T. D., et all, Electrophoresis 1999, 20, 1280–1300.
[12] Luckey, J. A., Norris, T. B., Smith, L. M., J. Phys. Chem. 1993, 97, 3067–3075.
[13] Luckey, J. A., Smith, L. M., Electrophoresis 1993, 14, 492–501.
[14] Izmailov, A., Yager, T. D., Zaleski, H., Darasch S., Electrophoresis 2001, 22, 1906–1914.
[15] Brigham, E. O., The Fast Fourier Transform, Prentice-Hall, Englewood-Cliffs, 1974.
[16] Barron, A. E., Heller, C., in: Heller, C. (Ed.), Analysis of Nucleic Acids by Capillary Electrophoresis, Vieweg Verlagsgesellschaft, Weisbaden 1997, pp. 93–124.

What is claimed is:

1. A method for creating a simulated electrophoretic trace for use in sequencing a sample polynucleotide sequence, comprising the steps of
   (a) obtaining an input file containing an input base sequence, derived from an expected reference base sequence independent of the sample polynucleotide sequence, comprising a string of letters (A, C, G and/or T) in an order corresponding to the input base sequence;
   (b) modifying the input file using one or more functions to introduce distortions associated with (1) changes in peak intensity as a function of base number; (2) peak shape as a function of base number; (3) peak skew; (4) spacing between peaks; (5) background; (6) noise; (7) spectral cross-talk; (8) instrumental effects and/or (9) gel electrophoresis effects to produce a modified file representing a simulated electrophoretic trace.

2. The method of claim 1, wherein the input file is a text file.

3. The method of claim 1, wherein the input file is an experimentally recorded data trace recorded from an automated DNA sequencer.

4. The method of claim 1, wherein peak intensity in the simulated electrophoretic trace is modified as a function of base number in accordance with the function $$I_i(N) = I_{oi} \exp(-\beta_i N)$$

where i=type of base (A, C, G, T), N=base number, $I_i(N)$=intensity of ladder of type i as function of base number, $I_{oi}$=intensity of unextended primer within ladder of type i, and $\beta_i$=exponential decay parameter for the intensity of ladder of type i.

5. The method of claim 1, wherein peak shape in the simulated electrophoretic trace is modified as function of base number in accordance with the function $$I_N(t) = \frac{I_{N0}}{\sigma_N \sqrt{2\pi}} \exp\left(\frac{-(t-t_N)^2}{2(\sigma_N)^2}\right)$$

where $I_N(t)$=fluorescent intensity at time t, within the peak corresponding to base number N; $I_{N0}$=intensity maximum of this peak, $\sigma_N$=width of peak (Gaussian standard deviation), and $t_N$=center of the peak.

6. The method of claim 1, wherein spacing between peaks in the simulated electrophoretic trace is modified as a function of base number in accordance with the function $$t(N) = t_0 + \sum_i a_i N^i \qquad (4)$$

where $a_i$ are the polynomial coefficients, and i is the degree of the polynomial.

7. An apparatus for generating a simulated electrophoretic trace comprising a programmed computer processor connected for communication with a storage device having stored thereon a set of program instructions for carrying out the method of any of claims 1–6.

8. A method for determining the nucleotide sequence of a sample polynucleotide, comprising the steps of
   (a) generating a simulated base sequence by (i) obtaining an input file containing an input base sequence derived from an expected reference base sequence independent of the sample nucleotide sequence, comprising a string of letters (A, C, G and/or T) in an order corresponding to the input base sequence, and (ii) modifying the input file using one or more functions to introduce distortions associated with (1) changes in peak intensity as a function of base number, (2) peak shape as a function of base number, (3) peak skew, (4) spacing between peaks, (5) background, (6) noise, (7) spectral cross-talk, (8) instrumental effects, and/or (9) gel electrophoresis effects, to produce a modified file representing a simulated electrophoretic trace;
   (b) obtaining an experimental base sequence of a sample;
   (c) comparing the experimental base sequence of the sample with the simulated base sequence; and
   (d) correlating bases of the experimental base sequence with corresponding bases of the simulated base sequence, to thereby determine the sequence of the sample.

* * * * *